United States Patent [19]

Speidel

[11] 4,012,604
[45] Mar. 15, 1977

[54] MICROPHONE FOR THE TRANSMISSION OF BODY SOUNDS

[76] Inventor: Blasius Speidel, Hochmeisterstrasse 244, 7455 Jungingen, Germany

[22] Filed: June 17, 1975

[21] Appl. No.: 587,684

[30] Foreign Application Priority Data

June 18, 1974 Germany .................. 2429045

[52] U.S. Cl. .................. 179/121 C; 179/1 ST; 179/110 A; 128/2.05 S; 181/171
[51] Int. Cl.² .................. H04R 1/46; H04R 7/22
[58] Field of Search .......... H04R/17/02; 179/1 ST, 179/121 C, 110 A, 110 D, 110 F; 128/2.05 E, 2.05 S, 2.05 P; 181/126, 129, 131, 137, 172, 171; 310/8.3, 8.5

[56] References Cited

UNITED STATES PATENTS

| 392,763 | 11/1888 | Tainter | 181/171 |
| 1,236,476 | 8/1917 | Penney | 181/171 |
| 2,121,779 | 6/1938 | Ballantine | 179/121 C |
| 2,702,354 | 2/1955 | Chordening | 128/2.05 P |
| 3,157,246 | 11/1964 | Howell | 181/137 |
| 3,182,129 | 5/1965 | Clark et al. | 179/1 ST |
| 3,387,149 | 6/1968 | Young | 128/2.05 S |
| 3,682,161 | 8/1972 | Alibert | 179/1 ST |
| 3,767,004 | 10/1973 | Liebscher | 181/172 |
| 3,868,954 | 3/1975 | Ueda | 179/1 ST |

FOREIGN PATENTS OR APPLICATIONS

| 1,343,675 | 10/1963 | France | 179/1 ST |
| 1,155,264 | 10/1963 | Germany | 179/110 A |
| 488,007 | 12/1953 | Italy | 179/1 ST |
| 307,787 | 8/1955 | Switzerland | 179/1 ST |

Primary Examiner—George G. Stellar
Attorney, Agent, or Firm—Joseph A. Geiger

[57] ABSTRACT

A microphone for the transmission and conversion of low frequency body sound signals, characteristic of blood pressure conditions, the microphone featuring a Seignette salt crystal wafer as a transducing element, a foamed body as a transmitting element, a vibrating mass on the microphone membrane, and a deflection-limiting safety plate. The membrane carries a contact-focusing touch plate, and the entire housing is enveloped in a sound insulating rubber jacket.

33 Claims, 15 Drawing Figures

MICROPHONE FOR THE TRANSMISSION OF BODY SOUNDS

BACKGROUND OF THE INVENTION

1. Field of the Invention

The present invention relates to microphones, and more particularly to a microphone for the transmission and conversion of low frequency body sounds, the microphone being of the type having a shallow housing whose open side carries a peripherally clamped membrane interacting with a Seignette salt crystal wafer arranged inside the housing, through the intermediate of a transmitter body.

2. Description of the Prior Art

Microphones of the above-mentioned type are used with great success for the transmission of body sounds in conjunction with blood pressure measuring devices, the microphone being normally arranged on the inside of the measuring sleeve of the blood pressure measuring device, so that it is placed in contact with the limb on which the blood pressure is measured. In certain situations, however, such a body sound microphone is not arranged directly on the measuring sleeve, but mounted on a microphone adapter attached to the measuring sleeve, and in other, rare, cases, the microphone may be mounted on a separate implement which is fastened to the limb in question independently of the measuring sleeve of the blood pressure measuring device. Microphones for the transmission of body sounds serve for the determination of blood pressure characteristics in the person which is being examined, the microphone being capable of transmitting the so-called Korotkoff noises which are generated by the blood circulation downstream of the measuring sleeve, when the air pressure in the sleeve reaches a certain range of excess pressure. The microphone transforms these sounds into electronic signals which are then transmitted to the blood pressure measuring device and which, following appropriate amplification, can be used to affect certain controls on the measuring device, by operating certain switching functions, depending upon the design of the blood pressure measuring device.

The principal component of such a body sound microphone is a Seignette salt crystal wafer of square outline which is clamped elastically on three of its corners by means of suitable clamping blocks attached to the microphone housing in such an orientation that the fourth corner of the crystal wafer is positioned at a place that coincides approximately with the geometric center axis of the microphone housing and of the attached membrane. Between the lower side of this membrane and the upper side of the crystal wafer is normally arranged a transmitter body of solid plastic material which transmits the vibrations induced in the membrane by the body sounds to the free corner of the crystal wafer. The latter thus acts as a crystalline flexing member. The deflection of the crystal wafer creates piezoelectric voltage variations which are picked up by leads connected to the two sides of the crystal wafer, which leads transmit the signals to a signal amplifier.

Seignette salt crystal wafers have proved to have the highest presently obtainable signal transmission efficiency. They also have a serious shortcoming, however, in that they are very sensitive to mechanical stress. Because their signal transmitting efficiency is inversely related to the thickness of the wafer, the risk of fracture of such a wafer increases with increasing transmission quality. For this reason, Seignette salt crystal wafers are not presently used in the manufacture of body sound microphones, inspite of their excellent piecoelectric characteristics. In their place are presently used ceramic piezoelectric receivers of approximately the same shape, in approximately the same mounting arrangement.

Piezoelectric ceramic wafers have a much greater resistance against mechanical stress. Their resistance is adequate for their incorporation in blood pressure measuring devices, without the need for additional safety precautions. However, the comparatively reduced risk of fracture of piezoelectric ceramic wafers is accompanied by a much reduced efficiency of transmission, as compared to the Seignette salt crystal wafer. The former type of wafer therefore necessitates a much greater signal amplification. This need, in turn, brings with it the problem that the natural capacitance of the connection to the amplifier becomes an influential part of the transmitted signal. When such a receiver element is interchanged, or when the connection to the amplifier is replaced, there results a change in the impedance which makes it necessary in each case to rebalance the input amplifier. In order to equalize the changes in capacitance among different receivers, known instruments are equipped with a preamplifier in the receiver housing, the preamplifier being electrically interposed between the ceramic wafer and the near end of the connecting leads to the amplifier. This preamplifier does not equalize capacitance changes in the connecting leads, however, so that the latter have to be separately balanced. In a situation where a blood pressure measuring device is equipped with several measuring sleeves and associated receivers, and where the measuring sleeves are used interchangeably, it becomes necessary to rebalance the input amplifier in the instrument, whenever a different measuring sleeve is used, because there exist unavoidable manufacturing tolerances between the various preamplifiers in the different microphones.

SUMMARY OF THE INVENTION

It is a primary objective of the present invention to provide a body sound microphone which is adapted for taking advantage of the excellent transmission characteristics of a Seignette salt crystal wafer, and in which the risk of fracture of the crystal wafer is greatly reduced.

The present invention proposes to attain the above objective by suggesting a body sound microphone of the earlier-mentioned type which is characterized in that the transmitter body which links the crystal wafer to the membrane is a foamed body.

The use of foamed material for the transmitter body renders the latter elestically yielding as a protection of the crystal wafer, even under the influence of excessive mechanical forces which may be applied to the membrane. On the other hand, its filigree structure is capable of providing an excellent transmission of the body sound signals originating from the Korotkoff noises from the membrane to the Seignette salt crystal wafer, without damping, and hence without distortion. The wafer transforms these signals into electronic signals with a high piezoelectric efficiency. Such a body sound microphone, because it has these extraordinary qualities, does not require any preamplifier inside the microphone housing. This also means that the natural capacitancies of the receiver and of the connection to the signal amplifier are so small in relation to the signal amplitude that several body sound microphones and/or their connecting lines can be interchanged against each other without concern, even where there are considerable differences in length from one connecting line to the other. This affords the further advantage of making it possible for the novel body sound microphones to be used in conjunction with remote measuring installations, without the need for special adaptive procedures, as when the body sound microphone and the related measuring sleeve are used in one room, while the signal amplifier and the other components of the blood pressure measuring device are located in an adjacent room.

The use of foamed material for the transmitter body also eliminates a previously encountered electrostatic problem which is present, when the body sound microphone is equipped with a transmitter body of solid plastic and which makes itself felt, when the signal converting element is a Seignette salt crystal wafer with a high degree of conversion efficiency. The membrane of the body sound microphone has a tendency to pick up an electrostatic charge resulting from an ion phase shift in the body tissues caused by certain circulation characteristics. This electrostatic charge on the membrane is then transmitted by a solid body, especially by a solid body of plastic material, so that it creates a base charge on the molecular crystalline structure of the Seignette salt crystal, thereby reducing its sensitivity by decreasing its output performance to a point where the lower frequencies are strongly dampened, if not completely suppressed. And because the Korotkoff body sounds lie in a low frequency range, such a reduced electrostatic conductivity of the foamed body has proved to be very advantageous in comparison to a solid plastic body.

A particularly advantageous embodiment of the body sound microphone of the invention features an arrangement in which a cylindrical vibrating mass of plastic material is arranged between the normally cylindrical foamed body and the membrane. Its presence noticably improves the transmission characteristics of the membrane, especially in the low frequency range, so that the excellent sound transmission quality of the foamed transmitter body is also utilized on the membrane interface. It was furthermore found to be advantageous to provide an adhesive bond between the foamed body and the Seignette salt crystal wafer on the one side, and the plastic vibrating mass on the other side, as well as between the latter and the membrane. This bilateral bond between the foamed body and the crystal wafer on the one side, and the membrane on the other side, through the intermediate of the vibration mass, also precludes any risk that settling of the foamed body may take place under the prolonged application of high mechanical loads.

A still further advantageous feature of the invention relates to an embodiment of the body sound microphone which includes an interior shoulder on the side wall of the housing which carries a safety plate underneath the membrane, the safety plate having an appropriate aperture for the transmitter body. The optimal spacing between the upper side of the safety plate and the lower side of the membrane was found to be between 0.7 and 0.8 mm. This arrangement assures that the membrane, even under inadvertent or improper handling of the body sound microphone, cannot be deflected beyond the abutment position with the safety plate, which stops the membrane from moving any further toward the inside of the microphone housing. This feature represents a positive safety against damage. For, inspite of the considerable compressibility of the foamed body, the latter might otherwise, under certain circumstances, create enough strain on the fragile Seignette salt crystal wafter to break it. The proposed optimal spacing between the membrane and the safety plate is such that the former is free to respond to all body sound vibrations.

An electrically conductive membrane, or a membrane carrying conductive material, is adequate to remove all electrostatic charges which the membrane may receive from the adjacent tissue portions, thereby reinforcing the shielding effect of the foamed body against the transmission of these electrostatic charges to the crystal wafer. It is further possible to obtain this result with a thin metal strip attached to the inside of the membrane. It has been found that the optimal dimensions for such a strip are in the area of 10 mm width and 25 mm length. The kind of metal utilized for this strip is preferably brass, which has shown an optimal performance because of its superior suitability for electrostatic transmission. Such a metal strip, having a thickness of 0.06 mm, for example, does not impede the sound transmission characteristics of the membrane itself.

The transmission characteristics of the membrane of the proposed body sound microphone are enhanced in an embodiment which features a peripheral clamping configuration for the membrane using opposing circular knife edge profiles arranged on the rim of the housing wall and on the cooperating clamping ring. It is also possible, however, to provide the clamping ring as a two-part assembly, using a separate edge ring carrying one knife edge and an intermediate self-curing plastic filler between this ring and the collar element of the clamping collar assembly, so that any dimensional variations due to manufacturing tolerances, or due to a not precisely parallel assembly between the two knife edges is compensated for and the membrane is clamped on its entire periphery with a precisely even clamping force.

A still further possibility of enhancing the excellent transmission characteristics of the membrane of this body sound microphone relates to a feature of this invention which suggests that the support surface for the membrane on the end face of the lateral housing wall and the cooperating clamping face of the collar have the outline of a straight frustum whose base faces toward the housing bottom and whose enclosed angle is an obtuse angle of preferably 170°. The opposing clamping faces, being accordingly parallel, but 5° inclined from the plane of the flat membrane, cause the latter to be preloaded along its periphery so that it assumes a slightly convex, outwardly bulging shape. The membrane retains this preload-induced shape to a large degree, even when the body sound microphone is placed against some part of the body, the transmission characteristics remaining unaffected for all practical purposes, by changes in the static forces acting on the receiver.

A stil further advantageous feature of the invention suggests the application to the outside of the membrane of a touch plate made of silicone rubber or of a comparable material, preferably in the shape of an ellipsoidal sector, in order to obtain a certain focusing of the membrane receptivity onto a particular artery, so that the excellent transmission characteristics of the novel body sound microphone can also be utilized to advantage, when the measurements are made on limbs which are either comparatively small in relation to the dimensions of the microphone, as far as the membrane size is concerned, as is the case with children or with adults having limbs emaciated by illness, or where the measurements are made on particularly muscular and/or tendinous tissue structures, i.e., in all cases where the fatty tissues which facilitate the focusing of the body sound microphone are more or less missing.

Another advantageous feature of a preferred embodiment of the invention suggests a body sound microphone which has a metallic housing made of aluminum, for example, whose bottom and side walls are enclosed within a cup-shaped jacket of plastic material, with a space between the jacket and the housing walls which is filled with a filler material. This configuration offers an acoustic insulation of the housing of this sensitive body sound microphone against other parts of the equipment to which it may be connected, such as the measuring sleeve or a special attachment or handle, for instance, thereby precluding the formation of any sound bridges over which undesirable interference signals from environmental noise sources can reach the membrane.

A still further advantageous feature of the body sound microphone of the invention relates to the aforementioned acoustically insulating jacket, as far as its cross-sectional outline is concerned, the invention suggesting a housing shape having a large radius at its bottom edge and/or that the jacket has a bottom portion whose outer side is convexly curved in the shape of a spherical sector or an ellipsoidal sector. This bulge may involve a portion of the bottom wall or the entire bottom wall of the housing. Such a shape is advantageous when the body sound microphone is applied against a limb by means of a blood pressure measuring sleeve, for thus permitting the latter to snugly engage the back side of the body sound microphone, so as to ensure correct blood pressure measurements, by assuring an even contact between the measuring sleeve and the limb. This configuration has the advantage that it eliminates any large empty spaces between the measuring sleeve and the body sound microphone, thereby preventing the creation of rubbing noises, or the formation of folds on the measuring sleeve which could likewise lead to extraneous noises. This design of the body sound microphone, which is particularly easy to realize in conjunction with a cup-shaped jacket of plastic material, can of course also be utilized on the metallic microphone housing itself.

It was found that a particularly suitable material for the foamed body which is interposed between the membrane and the Seignette salt crystal is a polyester foam of the type MB, having the following physical characteristics:

| | |
|---|---|
| density: | 22 kg/m³; |
| indentation hardness: | 40% – 20 kp, per DIN 53576; |
| compression hardness per cm²: | 40% – 40 kp, per DIN 53576; |
| tensile strength: | 1.5 kp per cm², per DIN 53571; |
| failure elongation in %: | > 200% per DIN 53571; |
| residual compressive deformation: | 50% over 20, per DIN 53571; and |
| micropores: | approx. 0.09 mm dia. |

A particularly suitable plastic material for the cylindrical vibrating mass, which is disposed between the membrane and the foamed body, is a hard PVC, per DIN Standard No. 4077, having the following physical characteristics:

| | |
|---|---|
| impact resistance: | unbroken at 0° C, per DIN 52433; |
| notched bar impact response: | 4 cm kp/cm² (with bars of 20–70 mm dia.); |
| failure elongation: | > 100%; |
| tensile strength: | > 500 kp/cm²; |
| modulus of elasticity: | 300000 kp/cm²; and |
| compressive strength: | 800 kp/cm². |

A membrane of 36.6 mm diameter, having a thickness of 0.3 mm, was found to give excellent results, using as a particularly suitable membrane material a hard epoxy glass fiber fabric (a) fiber glass fabric with epoxy resins per DIN Standard No. 7735), with the following physical characteristics:

| | |
|---|---|
| flexural strength: | > 3500 kp/cm², per DIN 53452; |
| impact resistance: | > 100 cm kp/cm²; |
| tensile strength: | 2200 kp/cm²; |
| compressive strength parallel to grain: | > 4000 kp/cm²; |
| compressive strength across grain: | > 2000 kp; |
| splitting resistance: | > 300 kp; |
| modulus of elasticity: | 180000 kp/cm²; |
| continuous heat resistance: | 130° C; |
| raw density: | 1.7 to 1.9 gr/cm³; and |
| surface resistance: | > $10^{12}$ ohms. |

The touch plate to be attached to the outer side of the membrane is preferably of silicone rubber, for which the optimal physical characteristics are those of a two-component silicone rubber mass, like one which is commercially available from Wacker-Chemie, Munich, Germany, containing the following components: silicone rubber filler RTW, listed under part No. KTR-2264 028 143 and a curing agent TK, listed under part No. KTR-801.

In conjunction with the above-mentioned optimal dimensions and suggested optimal physical characteristics of the component materials for the membrane, plastic vibrating mass, and foamed transmitter body, the following dimensions are preferably chosen for the Seignette salt crystal wafer: length and width equal to 12.5 mm, tickness equal to 0.6 mm.

A suitable material for the cup-shaped jacket surrounding the microphone housing, if one is used, would be polyamide. A suitable material for the filler occupying the space between the jacket and the microphone housing would be a silicone rubber mass having the physical characteristics of a silicon rubber mass which is commercially available from Wacker-Chemie, Munich, under the trade name "Elastosil 59".

BRIEF DESCRIPTION OF THE DRAWINGS

Further special features and advantages of the invention will become apparent from the description following below, when taken together with the accompanying drawings which illustrate, by way of example, several embodiments of the invention, represented in the various figures as follows.

DESCRIPTION OF THE PREFERRED EMBODIMENTS

Figure 1:
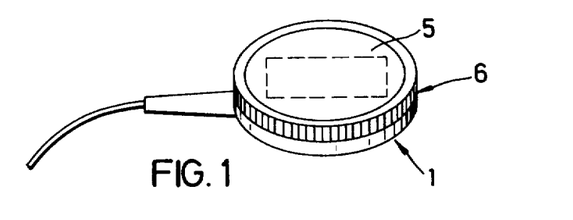
FIG. 1 shows, in a perspective representation, a body sound microphone representing an embodiment of the invention.
Figure 2:
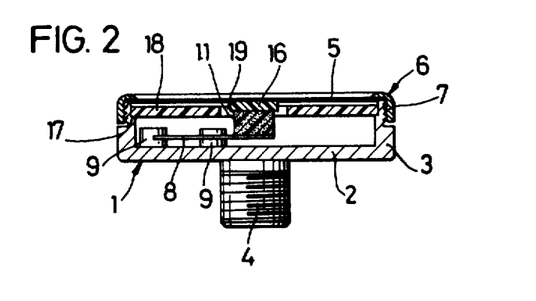
FIG. 2 shows the microphone of FIG. 1 in an enlarge elevational cross section.
Figure 3:
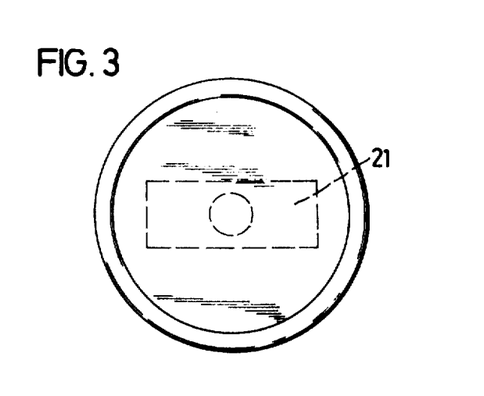
FIG. 3 shows the microphone of FIGS. 1 and 2 in a plan view.

Referring to FIGS. 1 and 2 of the drawing, there is illustrated a microphone for the transmission of body sounds, in accordance with the present invention, which includes a cup-shaped housing 1, preferably made of aluminum, the housing having a generally flat disc-like bottom 2 and a short tubular side wall 3. From the lower side of the bottom 2 extends, as an integral part of the housing 1, a threaded connecting stud 4, by means of which the body sound microphone is attachable to the measuring sleeve, or some other suitable supporting implement, of a blood pressure measuring device. The opposite end of the housing 1 is covered with a membrane 5 which is supported on the rim of the housing side wall 3, where it is clamped in place by means of a clamping collar 6. The clamping collar includes a flange portion 7 with a female thread engaging a matching male thread on the outer side of the housing side wall 3.

Figure 4:
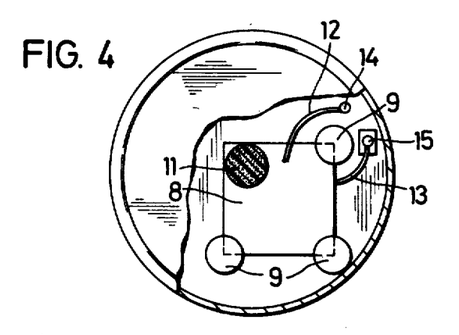
FIG. 4 is a representation similar to FIG. 3, showing portions of the microphone removed.

Inside the microphone housing 1 is arranged a Seignette salt crystal wafer 8 which, as can best be seen in FIG. 4, is of square outline and is held in place by means of severl cylindrical mounting blocks 9. These mounting blocks are arranged on three of its four corners, having suitable lateral grooves for the positioning of the crystal wafer 8. The mounting blocks 9 are made of an insulating material and are glued to the inside of the housing bottom 2 in such a way that the free fourth corner of the crystal wafer 8 is positioned underneath the circular contact area of a transmitter body 11. To the upper and lower surfaces of the crystal wafer 8 are soldered thin metallic ribbons 12 and 13, respectively, which lead to electrical terminals 14 and 15. The terminal 14 establishes electrical contact with the bottom 2 of the housing while the terminal 15 is electrically insulated thereagainst.

The transmitter body 11 is cylindrical in shape and made of a foam material, its optimal dimensins being 3 mm height, or, better still 4 mm, with a diameter of 6 mm. The foamed body 11 is glued to the crystal wafer 8.

The microphone membrane 5 includes on its inwardly facing side a vibrating mass 16 which is glued to the center area of the membrane. Optimally, this vibrating mass is 3.5 mm high and 6 mm in diameter. It is made of solid synsthetic plastic, the latter being preferably a hard plastic, such as, for example, a so-called duroplast, or a hard PVC. The vibrating mass 16 serves to tune the vibration responsiveness of the membrane 5 to the transmission of the body sound signals resulting from the Korotkoff noises, whose important frequency range is comprised between zero and 150 cycles, more particularly in the frequency range of 17 to 75 cycles per second. On its side facing away from the membrane, the vibrating mass 16 is glued to the foamed transmitter body 11, in order to eliminate the otherwise present risk that the body 11 could undergo settling, should a major mechanical load to applied to it, via the membrane 5, for an prolonged period of time.

On the inner side of the housing side wall 3 is arranged a shoulder 17 carrying a safety plate 18 engaging the bore above the shoulder with a tight fit. This safety plate has a central aperture 19 through which extends the vibrating mass 16 and the transmitter body 11. The safety plate 18 is likewise made of plastic material, using, for example, so-called pertinax. The level of the shoulder 17 inside the housing 1 is preferably such that a spacing of between 0.7 and 0.8 mm between the upper side of the safety plate 18 and the lower side of the membrane 5 is obtained. This distance is sufficient to give the membrane 5 full freedom to undergo such deformation as may result from the contact with a limb, augmented by the vibratory displacements resulting from the body sound signals. However, when an excessive force is inadvertantly applied to the membrane 5, the latter is prevented from deflecting inwardly beyond abutment against the safety plate 18, so that the sensitive inner components of the microphone are effectively protected. In the absence of such a safety plate, it could happen that, in spite of the considerable compressibility of the foamed transmitter body 11, the latter would exert sufficient pressure against the crystal wafer 8 to fracture the latter.

The membrane 5 may further include a metal strip 21 attached to its inner side. This strip is rectangular in shape, preferably 25 mm long and 10 mm wide, having a thickness of 0.06 mm. A preferred material for this strip is semi-hard brass sheet. The purpose of this metal strip 21 is to remove from the membrane 5 any electrostatic charges that may be generated by the tissue parts against which the body sound microphone makes contact, thereby shielding the transmitter body 11, and further enhancing its insulating characteristics. This is important, in order to prevent the establishment of a base charge on the molecular crystalline structure of the Seignette salt crystal wafer 8. Such a charge would greatly dampen, if not completely suppress, the output performance of the crystal wafer 8, especially in the low frequency range which is of particular importance in connection with the proposed use of the microphone.

Figure 5:
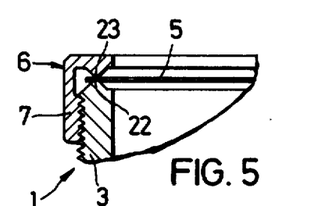
FIGS. 5 through 8 show, in enlarged detail, the peripheral attachment of the microphone membrane in five different embodiments.
Figure 5A:
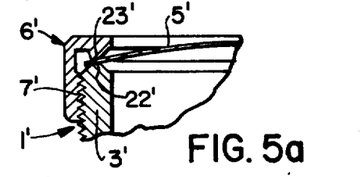

Several modes for peripherally clamping the membrane 5 between the microphone housing 1 and a clamping collar 6 are illustrated in the enlarged fractional representations of FIGS. 5 through 8. In FIG. 5 is shown a modified embodiment in which the membrane support takes the form of a circular knife edge 22 on the end face of the housing side wall 3. The included angle of the knife edges shown in FIGS. 5 through 8, is shown much more pointed than would normally be desirable, in order to better illustrate the configuration in the drawing. The clamping collar 6 has a similar oppositely facing circular knife edge 23, the periphery of the membrane 5 being clamped between the opposing knife edges 22 and 23. FIG. 5a shows a configuration in which the membrane 5' is convexly preloaded by a slightly inclined orientation of the opposing knife edges 22' and 23'.

Figure 6:
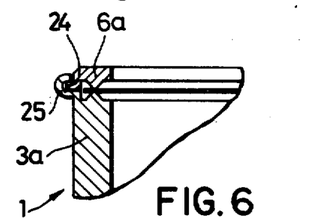
Figure 7:
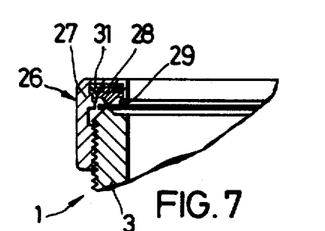
Figure 8:
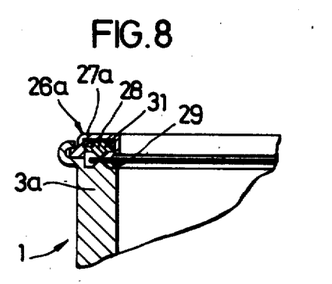

The embodiment represented by FIGS. 1 and 5 has a one-piece clamping collar 6 whose tubular flange portion 7 is threaded to engage a matching outside thread on the side wall 3 of the microphone housing. The embodiment of FIG. 6 shows a clamping collar 6a which is retained against the housing side wall 3a by means of two cooperating flanges 24 and 25, the latter being crimped upwardly and inwardly over the former. The modified embodiments of FIGS. 7 and 8 show two-piece clamping collars 26 and 26a, respectively. Each clamping collar has a collar element 27, or 27a, engaging the housing side wall either with matching threads (FIG. 7), as are also used in the version of FIG. 5, or with crimped flanges (FIG. 8), as are likewise used in FIG. 6, while a separate edge element 28 is in each case mounted inside the collar element. For this purpose, the latter has an annular groove 29, receiving therein the edge element 28, the latter being provided with anchoring formations on its side facing away from the knife edge. These anchoring formations may be grooves or ridges, or preferably a dovetail profile like the one which is shown in the drawing. Just prior to final assembly of the edge element 28 to the clamping collar element 27 or 27a, a selfcuring plastic mass 31 is applied to the annular groove 29, whereupon the edge element 28 is inserted into the groove. The assembled clamping collar is then attached to the completely assembled microphone, thereby holding the membrane 5 in place. The initial resiliency of the plastic mass 31 interposed between the collar element 27 or 27a, respectively, and the edge element 28 thus assures that the membrane is clamped with a virtually absolutely even clamping force, the condition remaining intact after the plastic mass 31 has cured into a hard layer. This assembly method represents a convenient way of compensating for any manufacturing tolerances of the component parts and/or inaccuracies in the assembly of these parts, which would otherwise be detrimental to the desired even clamping of the membrane 5.

Figure 9:
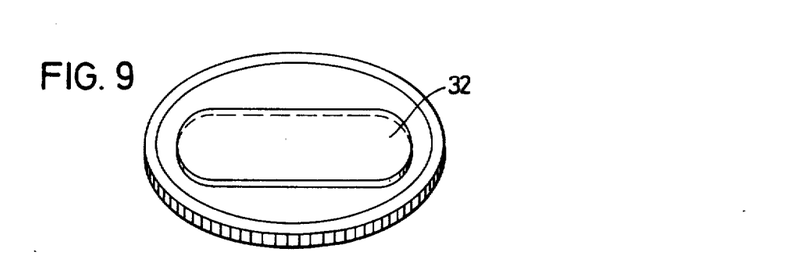
FIG. 9 is a perspective view of a clamping ring and membrane for the microphone of FIGS. 1–4, modified to include a touch plate.
Figure 10:
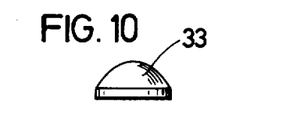
FIGS. 10 and 11 are a front view and a side view, respectively, of a modified touch plate for the membrane of FIG. 9.
Figure 11:
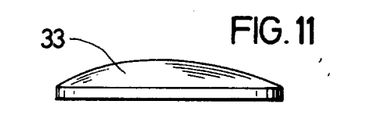

As an additional component part for the body sound microphone of the invention, there may be provided on the outer side of the membrane 5 a touch plate 32 of silicone rubber, or of some comparable material, a possible arrangement being shown in FIG. 9. This touch plate 32 is preferably of oblong, disc-like shape. An advantageous modification of the touch plate is shown in FIGS. 10 and 11, where the touch plate 33 has the shape of a sector of a minor-axis ellipsoid, FIG. 10 showing a portion of the generating ellipse, about whose minor axis the latter rotates, while FIG. 11 shows a portion of the circular equator of this ellipsoid. This kind of additional touch plate 32 or 33 makes it possible to engage the comparatively large membrane against rather thin limbs, as would be the case with children's limbs, or with limbs of adults that ae emaciated from illness, or when the limb on which the measurements are taken has especially muscular or tendinous tissue. In these cases, the touch plate makes it possible to improve the focusing of the microphone onto a particular artery, when the body sound microphone is mounted on the inside of a blood pressure measuring sleeve which is attached to the particular limb. If the touch plate 32 or 33 is made of a material other than silicone rubber, it should be ascertained that the natural sound conductivity of the material corresponds to the frequency spectrum of the Korotkoff noises. The material should under no circumstances act as a damper in this frequency range.

Figure 12:
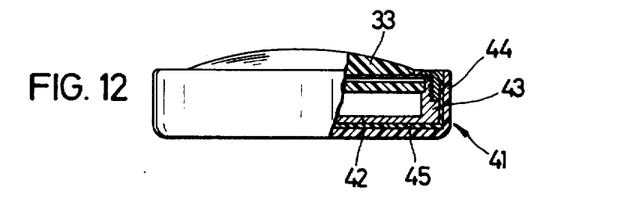
FIG. 12 shows a body sound microphone, partially cross-sectioned, representing another embodiment of the invention.

In FIG. 12 of the drawing is illustrated a further modified embodiment of the invention, showing a body sound microphone having a cup-shaped housing 41 with a disc-shaped flat body 42 and a tubular side wall 43, generally similar to those of the earlier-described embodiment. The lower side of the housing bottom 42 is in this case smooth, the threaded connecting stud of the earlier embodiment having been omitted. On the other hand, the microphone housing 41 is surrounded by a cup-shaped jacket 44 of polyamide, having a wall thickness of at least 1 mm and sourrounding the housing 41 in the area of its bottom 42 and of its side wall 43, by forming with the latter an intermediate space of at least 1 mm width. This intermediate space is occupied by a filler 45, preferably a silicone rubber filler having material characteristics like a silicone rubber filler which is commercially available from Wacker-Chemie, Munich, Germany, under the trade name Elastosil 59. In all other aspects, this embodiment of the body sound microphone corresponds to the earlier-described embodiment, reference being had to the latter for all other constructional details.

The body sounds microphone illustrated in FIG. 12 is adapted for attachment to the inside of a blood pressure measuring sleeve to which it is preferably permanently glued. In special cases, it is also possible to utilize this microphone without attaching it to the measuring sleeve, especially when it is intended to be interchangeable, in which case the microphone is simply inserted under the measuring sleeve, before the latter is being pressurized or the microphone may be mounted on a special implement or holder, being glued onto the latter, for example, whereby the special holder is detachably connected to the blood pressure measuring sleeve. One such possibility provides an appropriate pocket in the measuring sleeve into which the microphone holder is insertable, for instance, the body sound microphone itself remaining outside the pocket.

Figure 13:
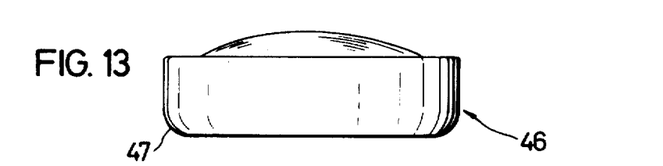
FIGS. 13 and 14 show body sound microphones similar to that of FIG. 12, with advantageously modified shapes.
Figure 14:
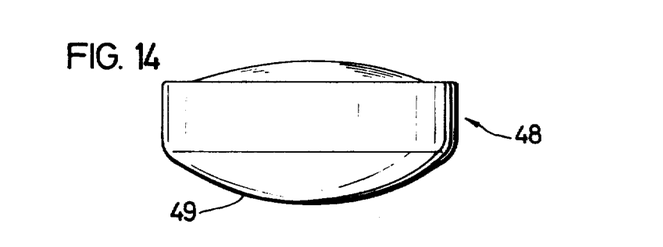

The embodiment of the body sound microphone featuring a cup-shaped plastic jacket surrounding a metallic microphone housing with an intermediate filler lends itself particularly well for additional advantageous modifications in regard to the overall shape of the body sound microphone. As can be seen in FIG. 13, there is shown a modified housing shape in which the jacket 46 has an outline with an especially large radius on the bottom edge 47 of the housing. A still further modification is shown in FIG. 14, where the jacket 48 indicates a convex curvature 49 at the housing bottom, which curvature may be derived from either a spherical sector or an ellipsoidal sector, whereby the major axis of the ellipsoid is parallel to the longitudinal axis of the touch plate 32 or 33, respectively, if such a plate is utilized.

It should be understood, of course, that the foregoing disclosure describes only preferred embodiments of the invention and that it is intended to cover all changes and modifications of these examples of the invention which fall within the scope of the appended claims.

I claim the following:

1. A microphone for the reception and conversion of low frequency sound, especially body sound signals, which can be used advantageously in conjunction with blood pressure measuring devices and the like, the microphone comprising in combination:

a cup-shaped microphone housing having a bottom and a generally tubular side wall with a rim defining an open upper end of the housing;

a circular membrane covering the open end of the housing and having a narrow peripheral edge portion clamped against the rim of the side wall;

a substantially flat flexural piezoelectric transducing wafer arranged inside the housing;

means for mounting the transducing wafer above the housing bottom, a distance from the membrane, and in substantially parallel alignment with the latter, the mounting means holding the transducing wafer in a cantilever fashion so as to allowing a portion thereof to flex freely in displacement alignment with the center of the membrane; and a resiliently compressible transmitter body interposed between and engaging both the membrane and said flexing portion of the wafer, at least a portion of the transmitter body, including the extremity with which it is engaged against the wafer, being of a cellular, foamed material suited for the transmission of low frequency sound vibrations.

2. A low frequency microphone as defined in claim 1 wherein the transducing wafer is a Seignette salt crystal wafer, having a generally quadrangular outline; and the wafer mounting means engages the wafer on three of its four corners, leaving the fourth corner free to flex with the membrane.

3. A low frequency microphone as defined in claim 2, wherein the Seignette salt crystal wafer is square in outline, having a side length of approximately 12.5 mm and a thickness of approximately 0.6 mm.

4. A low frequency microphone as defined in claim 2, wherein the transmitter body is a substantially cylindrical body of foamed synthetic plastic, having a diameter of approximately 6 mm and a height of approximately 4 mm.

5. A low frequency microphone as defined in claim 2, wherein the material of the transmitter body is a foamed polyester of the type MB, having the following physical characteristics:

| | |
|---|---|
| designation: | polyester foam; |
| type: | MB; |
| density: | 22 kg/m³; |
| indentation hardness: | 40% – 20 kp, per DIN 53576; |
| compression hardness per cm²: | 40% – 40 kp, per DIN 53576; |
| tensile strength: | 1.5 kp per cm², per DIN 53571; |
| failure elongation in %: | > 200%, per DIN 53571; |
| residual compressive deformation | 50% over 20, per DIN 53571; and |
| micropores | approx. 0.09 mm dia. |

6. A low frequency microphone as defined in claim 2, wherein the transmitter body comprises, in addition to a first body portion of said cellular foamed material, a second body portion which includes the extremity with which it is engaged against the membrane and which serves as a vibrating mass; and the vibrating mass is attached to the inner side of the membrane, near its center.

7. A low frequency microphone as defined in claim 6, wherein the vibrating mass is of solid plastic material, generally cylindrical in shape, and has a diameter of approximately 6 mm and a height of approximately 3.5 mm.

8. A low frequency microphone as defined in claim 6, wherein the material of the vibrating mass is a hard PVC per DIN Standard No. 4077, having the following physical characteristics:

| | |
|---|---|
| impact resistance: | unbroken at 0° C, per DIN 52433; |
| notched bar impact response: | 4 cm kp/cm² (with bars of 20 to 70 mm dia.); |
| failure elongation: | > 100%; |
| tensile strength: | > 500 kp/cm²; |
| modulus of elasticity: | 300000 kp/cm²; and |
| compressive strength: | 800 kp/cm². |

9. A low frequency microphone as defined in claim 6, wherein the vibrating mass is attached to the membrane by means of an adhesive bond; and the opposite end of the vibrating mass is attached to the formed portion of the transmitter body by means of an adhesive bond.

10. A low frequency microphone as defined in claim 1, werein the microphone membrane is a circular disc of approximately 0.3 mm thickness, having a diameter in the vicinity of 36.6 mm, and being made of an epoxy glass fiber fabric, known as fiber glass fabric with epoxy resins, per DIN Standard No. 7735, having the following physical characteristics:

| | |
|---|---|
| flexural strength: | > 3500 kp/cm², per DIN 53452; |
| impact resistance: | > 100 cm kp/cm²; |
| tensile strength: | 2200 kp/cm²; |
| compressive strength parallel to grain: | > 4000 kp/cm²; |
| compressive strength across grain: | > 2000 kp; |
| splitting resistance: | > 300 kp; |
| modulus of elasticity: | 180000 kp/cm²; |
| continuous heat resistance: | 130° C; |
| raw density: | 1.7 to 1.9 gr/cm³; and |
| surface resistance: | > 10¹² ohms. |

11. A low frequency microphone as defined in claim 1, further comprising:

membrane abutting means for limiting the inward deflection of the membrane under a large mechanical load inadvertantly applied to the membrane.

12. A low frequency microphone as defined in claim 11, wherein the membrane abutting means is a substantially rigid, centrally apertured safety plate mounted underneath the membrane, at such a distance therefrom that the membrane does not contact the safety plate during normal operation of the microphone.

13. A low frequency microphone as defined in claim 12, wherein the vertical distance between the safety plate and the membrane is such that the maximum inward deflection of the latter is limited to between 0.7 and 0.8 mm.

14. A low frequency microphone as defined in claim 12, wherein the microphone housing includes a shoulder on the inner side of the housing side wall; and the safety plate rests on said shoulder and is held in place by the housing side wall.

15. A low frequency microphone as defined in claim 1, wherein
the membrane includes means for diverting from the transmitter body and transducing wafer any electrostatic changes received from an extraneous source.

16. A low frequency microphone as defined in claim 15, wherein
the charge diverting means is constituted by electrical conductivity of at least a portion of the membrane.

17. A low frequency microphone as defined in claim 16, wherein
said electrically conductive portion of the membrane is a thin metal strip attached to the inner side of the membrane and extending across the center area of the latter.

18. A low frequency microphone as defined in claim 17, wherein
the membrane has a diameter of approximately 36 mm; and
the metal stip is a strip of semi-hard brass sheet of 0.06 mm thickness, being 25 mm long and 10 mm wide.

19. A low frequency microphone as defined in claim 1, further comprising:
means for peripherally clamping the membrane against the rim of the housing, said clamping means including a clamping collar engaging the membrane from the outside and cooperating with the housing rim to exert opposing substantially parallel oriented clamping forces against said peripheral edge portion of the membrane.

20. A low frequency microphone as defined in claim 19, wherein
the clamping collar and the housing rim have substantially parallel spaced opposing clamping faces with which they bear against said edge portion of the membrane; and said opposing clamping faces are geometrically defined by two shallow frustums having an included angle of approximately 170°, the clamping faces being accordingly oriented in such a way that they impose on a normally flat membrane an upwardly bulging convex outline, when clamped therebetween.

21. A low frequency microphone as defined in claim 19, wherein
the clamping collar and the housing rim have aligned oppositely facing circular knife edge profiles with which they bear against the peripheral edge portion of the membrane, thereby creating said clamping engagement.

22. A low frequency microphone as defined in claim 21, wherein
the clamping collar is an assembly of parts, including a collar element cooperating with the housing rim, an edge ring defining one of said knife edge profiles, and means for anchoring the edge ring against the collar element.

23. A low frequency microphone as defined in claim 22, wherein
the anchoring means of the clamping collar assembly includes: an annular inwardly facing groove in the collar element, adapted to receive therein the edge ring; an undercut cross-sectional contour on said ring; and an anchoring mass disposed in the space between said groove and said undercut edge ring contour; and
said anchoring mass is a self-curing hard mass, having been applied in a soft, uncured state during assembly of the microphone.

24. A low frequency microphone as defined in claim 1, further comprising
an outwardly protruding touch plate arranged on the outer side of the membrane, the touch plate covering an area that is smaller than that of the membrane, thereby presenting a reduced contact area to a limb against which the microphone may be held and thus focusing the receptivity of its membrane onto said reduced area; and wherein
the touch plate is of a material suited for the transmission of low frequency sound signals.

25. A low frequency microphone as defined in claim 24, wherein
the touch plate is adhesively bonded to the membrane; and
the material of the touch plate is a silicone rubber having physical characteristics approximating those of a two-component silicone rubber mass which is commercially available from Wacker-Chemie, Munich, Germany, and which consists of the components designated as silicon rubber filler RTV, Part No. KTR-2264 028 143 and curing agent TK, Part No. KTR-801.

26. A low frequency microphone as defined in claim 24 wherein
the shape of the touch plate approximates that of a sector of a body of rotation having an arched generatrix.

27. A low frequency microphone as defined in claim 26, wherein
the shape of the touch plate approximates that of a sector of a minor-axis ellipsoid, cut along a plane parallel to its rotational axis.

28. A low frequency microphone as defined in claim 1, wherein
the microphone housing is metallic and includes a sound-insulating jacket enveloping at least a major portion of the outer surface of the housing;
the housing and jacket define between them an intermediate space; and
said intermediate space contains a resilient filler material.

29. A low frequency microphone as defined in claim 28, wherein
the jacket is a cup-shaped body enveloping the bottom and side wall of the microphone housing; and
the material of the jacket is a silicone rubber mass having physical characteristics approximating those of a silicone rubber filler which is commercially available from Wacker-Chemie, Munich Germany, under the trade name Elastosil 59.

30. A low frequency microphone as defined in claim 28, wherein
the jacket is a cup-shaped body of polyamide, enveloping the bottom and side wall of the microphone housing; and
the wall thickness of the jacket is at least 1 mm.

31. A low frequency microphone as defined in claim 30, wherein
the intermediate space between the jacket and the housing is in all places at least 1 mm.

32. A low frequency microphone as defined in claim 28, wherein the jacket portion enveloping the bottom of the microphone housing has a rounded outline with a curvature approximating that of a sector of a body of rotation having an arched generatrix.

33. A low frequency microphone as defined in claim 32, wherein
the outline of said jacket portion approximates the curvature of a sector of a minor-axis ellipsoid, cut along a plane parallel to its rotational axis.

* * * * *